(12) United States Patent
Pya et al.

(10) Patent No.: US 10,751,456 B2
(45) Date of Patent: Aug. 25, 2020

(54) METHOD OF IMPLANTATION OF LEFT VENTRICULAR MECHANICAL ASSIST DEVICE HEARTMATE III

(71) Applicant: Joint-Stock Company "National Research Center for Cardiac Surgery", Astana (KZ)

(72) Inventors: Yuriy Pya, Astana (KZ); Serik Bekbossynov, Astana (KZ); Assel Medressova, Astana (KZ)

(73) Assignee: JOINT-STOCK COMPANY "NATIONAL RESEARCH CENTER FOR CARDIAC SURGERY", Astana (KZ)

( * ) Notice: Subject to any disclaimer, the term of this patent is extended or adjusted under 35 U.S.C. 154(b) by 59 days.

(21) Appl. No.: 15/940,028

(22) Filed: Mar. 29, 2018

(65) Prior Publication Data
US 2019/0298904 A1    Oct. 3, 2019

(51) Int. Cl.
| | | |
|---|---|---|
| *A61M 1/12* | (2006.01) | |
| *A61M 1/10* | (2006.01) | |
| *A61B 17/04* | (2006.01) | |
| *A61F 2/24* | (2006.01) | |

(52) U.S. Cl.
CPC ......... *A61M 1/122* (2014.02); *A61B 17/0482* (2013.01); *A61M 1/1008* (2014.02); *A61F 2/2409* (2013.01); *A61F 2220/0008* (2013.01); *A61M 1/1086* (2013.01)

(58) Field of Classification Search
CPC .................. A61M 1/10; A61M 1/1001; A61M 1/101–1036; A61M 1/12; A61M 1/122
See application file for complete search history.

(56) References Cited

U.S. PATENT DOCUMENTS

2004/0236170 A1    11/2004    Kim

FOREIGN PATENT DOCUMENTS

RU    2550047 C2    5/2015

OTHER PUBLICATIONS

Yarboro, Leora T et al. "Technique for minimizing and treating driveline infections." Annals of cardiothoracic surgery vol. 3,6 (2014): 557-62. doi:10.3978/j.issn.2225-319X.2014.09.08.*

(Continued)

*Primary Examiner* — Eugene T Wu
(74) *Attorney, Agent, or Firm* — Browdy and Neimark, PLLC

(57) ABSTRACT

The invention relates to medicine, namely to cardiac surgery.
The object of the invention is to raise the effectiveness of implantation of the HeartMate III left ventricular assist device by minimizing postoperative complications and improving the long-term results of device operation.
The HeartMate III left ventricular assist device is implanted in compliance with the phased nature of the procedure. The site of implantation of the outflow cannula is carefully selected.
The proposed method of implantation of the HeartMate III left ventricular assist device makes it possible to minimize the surgical causes of device thrombosis and bleeding, to avoid kinking of the outflow graft, to reduce the percentage of development of infection complications of the cable exit region, and thus to improve the long-term results of device operation.

5 Claims, 2 Drawing Sheets
(2 of 2 Drawing Sheet(s) Filed in Color)

(56) References Cited

OTHER PUBLICATIONS

Horvath et al. "Minimally invasive implantation of left ventricular assist device HeartWare HVAD". Cor et Vasa vol. 57, Issue 2, Apr. 2015, pp. e70-e74.*
Hanke et al. "In Vitro Evaluation of Inflow Cannula Fixation Techniques in Left Ventricular Assist Device Surgery". Artificial Organs, 41: 272-275. 2016. doi:10.1111/aor.12735.*
Pya et al. "Initial 3-year outcomes with left ventricular assist devices in a country with a nascent heart transplantation program." ESC Heart Fail. Mar. 2016;3(1):26-34. Epub Oct. 30, 2015.*
Feldman et al. "The 2013 International Society for Heart and Lung Transplantation Guidelines for mechanical circulatory support: executive summary." J Heart Lung Transplant. Feb. 2013;32(2):157-87. doi: 10.1016/j.healun.2012.09.013.*
Feldmann C. et al. (2017) Techniques for Driveline Positioning. In: Montalto A., Loforte A., Musumeci F., Krabatsch T., Slaughter M. (eds) Mechanical Circulatory Support in End-Stage Heart Failure. Springer. Jul. 15, 2017.*
Son et al. Effect of Tunneling Method on Driveline Infection: Looking Beyond the Silicone-Skin Interface (SSI) Registry. The Journal of Heart and Lung Transplantation, vol. 35, No. 4S, Apr. 2016.*
Matsumoto et al. Driveline Angle Is Crucial to Prevent Exit Site Infection in Patients with HeartMate II. The Journal of Heart and Lung Transplantation, vol. 35, No. 4S, Apr. 2016.*
Russell et al. HeartMate II LVAS: Patient Management Guidelines. Dec. 14, 2006.*
Schibilsky et al. Double tunnel technique for the LVAD driveline: improved management regarding driveline infections. J Artif Organs (2012) 15:44-48.*
Schmitto et al., Minimally invasive implantation: The procedure of choice, Operative Techniques in Thoracic and Cardiovascular Surgery, 21:65-78 (2016).
Adamson, et al., Principles of HeartMate II Implantation to Avoid Pump Malposition and Migration, Journal of Cardiac Surgery, 2015 pp. 296-299, vol. 30.
HeartWare Inc., HeartWare Ventricular Assist System, Instructions for Use, 2012, pp. 1-104.
Kirklin, et al., Eight annual INTERMACS report: Special focus on framing the impact of adverse events. The Journal of Heart Lung Transplantation, Oct. 2017; pp. 1080-1086, vol. 36, No. 10.
Krabatsch, et al., Different surgical strategies for implantation of continuous-flow VADs—Experience from Deutsches Herzzentrum Berlin, Ann Cardiothorac Surg, 2014, pp. 472-474, vol. 3(5).
Pawale, et al., Technique for implantation of HeartMate II left ventricular assist device with concurrent mitral and tricuspid valve repair, Ann Cardiothorac Surg., 2014, pp. 532-534, vol. 3(5).
Slaughter, et al., Clinical management of continuous-flow left ventricular assist devices in advanced heart failure, The Journal of Heart Lung Transplantation, Apr. 2010, vol. 29, nol. 4S, pp. S1-S39.
Soleimani, et al., Technique for Insertion of HeartMate II Left Ventricular Assist Device Inflow Cannula, Ann. Thorac. Surg., 2011, pp. 2001-2002, vol. 91.
Taghavi, et al., Surgical Technique Influences HeartMate II Left Ventricular Assist Device Thrombosis, Ann. Thorac. Surg., 2013, pp. 1259-1265, vol. 96.
Thoratec Corporation, HeartMate II LVAS, Left Ventricular Assist System, Instructions for use, 2009, pp. 1-197.
Thoratec Corporation, HeartMate 3TM, Left Ventricular Assist System, 2017, pp. 1-536.
Whitson, Bryan A., Surgical implant techniques of left ventricular assist devices: an overview of acute and durable devices, Journal of Thoracic Disease, 2015, pp. 2097-2101, vol. 7(12).

* cited by examiner

METHOD OF IMPLANTATION OF LEFT VENTRICULAR MECHANICAL ASSIST DEVICE HEARTMATE III

FIELD OF THE INVENTION

The invention relates to medicine, namely to cardiology, and can be used during implantation of left ventricular mechanical assist devices.

BACKGROUND

For satisfactory long-term results form use of left ventricular auxiliary devices, an enormous role is played by their correct positioning during surgery and maintenance of this position for the life of the patient (Adamson R. M., Mangi A. A., Kormos R. L., Farrar D. J., and Dembitsky W. P. Principles of HeartMate II Implantation to Avoid Pump Malposition and Migration. J Card Surg 2015; 30:296-299; doi: 10.1111/jocs.12478).

According to the 8th Annual Report INTERMACS (Interagency Registry for Mechanically Assisted Circulatory Support (Kirklin J. K., Pagani F. D., Kormos R. L., Stevenson L. W., Blume E. D., Myers S. L., Miller M. A., Baldwin J. T., Young J. B., and Naftel D. C. Eighth annual INTERMACS report: Special focus on framing the impact of adverse events. J Heart Lung Transplant 2017; 36:1080-1086), the data base of which does not include HeartMate III, some of the frequent complications are:

blood flow (16.24% in the first 3 months post surgery); infection (13.63%).

At the same time, for practically 50% of patients, artificial left ventricles are planned in the capacity of "destination therapy" (permanent treatment).

The basic reasons for a lethal outcome, according to the INTERMACS Report, are neurologic dysfunctions, polyorganic insufficiency, infections, disruption of function of the devices, and insufficiency of the right ventricle.

A method is known for implantation of the left ventricular mechanical assist device HeartWare, which includes the following operation stages of use [HeartWare Ventricular Assist System Instructions for Use. HeartWare, Inc. Authorized 2009]. The HeartWare device is implanted intrapericardially. Choose the site of implantation of the inflow cannula somewhat anteriorly to the apex of the left ventricle and roughly 2 cm laterally to the anterior interventricular branch. The inflow cannula must be positioned in the direction of the mitral valve and in parallel to the interventricular septum. The sewing cuff is fixed to the myocardium using 8-12 2-0 polypropylene sutures with synthetic pledges. Said sutures do not reach the left ventricular chamber. [Krabatsch T., Drews T., Potapov E., Weng Y., Pasic M., Hetzer R. Different surgical strategies for implantation of continuous-flow VADs—Experience from Deutsches Herzzentrum Berlin. Ann Cardiothorac Surg 2014; 3(5):472-474; doi: 10.3978/j.issn.2225-319X.2014.09.06], that is, they are positioned intramyocardially. Then a crosswise incision is made of the myocardium with a scalpel and further a circular opening is made with a special instrument. A visual inspection is made of the left ventricular chamber to eliminate possible causes of obstruction of the inflow cannula (thrombi etc.). The latter is joined to the sewing cuff. Using a wrench, the sewing cuff is tightened around the cannula until there is a "click." An anastomosis is formed between the outflow graft and the ascending aorta. Device driveline tunneling, air embolism prophylaxis, an increase in the speed of the HeartWare device, and disconnection of the cardiopulmonary bypass (CPB) are carried out.

One drawback of the known method of HeartWare implantation is that the anatomic selection of the region of implantation of the inflow cannula (orientation relative to the anterior interventricular branch and the cardiac apex in cm). Determining the location should also be done under the observation of transesophageal echo cardiography, since heart dimensions can vary among different patients, and thus also the distance of the incision from the anterior interventricular branch and cardiac apex. Second, when "sew then cut" technique is used, it is technically inconvenient to make the revision of the left ventricular chamber to check the presence of possible inflow cannula obstruction factors. Third, considering the fact that the sutures for suturing the sewing cuff are disposed intramyocardially, there are potential risks of obstruction of the inflow cannula by the margins of the myocardium from the intraventricular chamber not covered by the sutures.

A method is known for implanting the HeartMate II left ventricular mechanical assist device, which includes preperitoneal and intraperitoneal placement of a pump [1) HeartMate II LVAS. Sistema podderzhki levogo zheludochka. Instruktsii po primeneniyu. Thoratec Corporation, 2005. 2) Slaughter M. S., Pagani F. D., Rogers J. G., Miller L. W., Sun B., Russell S. D., Starling R. C., Chen L., Boyle A. J., Chillcott S., Adamson R. M., Blood M. S., Camacho M. T., Idrissi K. A., Petty M., Sobieski M., Wright S., Myers T. J., and Farrar D. J., for the HeartMate II Clinical Investigators. Clinical management of continuous-flow left ventricular assist devices in advanced heart failure. J Heart Lung Transplant 2010; 29:S1-S39]. With preperitoneal positioning, a pouch for the device is created superiorly to the posterior portion of the insertion of the rectus abdominis muscle and the transverse fascia and inferiorly to the rectus abdominis and the internal oblique muscles. This method can be more preferable for patients who already had surgical operations in the abdominal region or for patients with a short torso. The device is placed beyond the limits of the internal organs of the abdominal chamber, where intestinal adhesions are unlikely. With intra-abdominal placement the pump is inserted into the abdomen to the left superior abdominal quadrant. This method may be preferable for a patient with malnutrition, for whom the risk of pump erosion through the skin is significant. In addition, correct tunneling of the device driveline may prove impossible for this group of patients. After preparation of the pump pouch, the driveline is tunneled. An 8-mm skin coring punch is used to perforate the skin. A site for the cylindrical incision is chosen that is anterior to the apex and a few centimeters to the side of the left anterior descending artery. A revision of the left ventricular chamber is made.

Secure the sewing ring cuff with at least 12 horizontal mattress sutures of nearly the full thickness at a distance of approximately 1.5 cm from the edge of the incision. Some literature sources describe the following technique for implantation of the sewing cuff of the device HeartMate II [1) Pawale A., Plotkina I., Anyanwu A. C. Technique for implantation of HeartMate II left ventricular assist device with concurrent mitral and tricuspid valve repair. Ann Cardiothorac Surg 2014; 3(5):532-534; doi: 10.3978/j.issn.2225-319X.2014.08.11. 2) Soleimani B., Stephenson E. R., Pae W. Technique for insertion of HeartMate II left ventricular assist device inflow cannula. Ann Thorac Surg 2011:91:2001-2002]. Twelve "pi-shaped" sutures of Ethibond 3-0 with synthetic pledgets are placed. The first needle passes through the entire thickness of the myocardium at a distance of 1.5 cm from the edge of the incision. Then this same needle is passed back at a distance of 2-3 mm from the edge of the incision from the endocardium to the epicardium. According to the authors, this technique makes it possible to reduce the incidence of development of postoperative bleeding. The outflow cannula is joined to the apical sewing ring and reinforced with ligatures. At its proximal end, the sealed drainage implant is connected to the drainage bend of the pump. An anastomosis is created between the outflow graft and the ascending aorta. De-airing is carried out, the HeartMate II device is activated and the CPB pump is turned off.

Defects of the pre-abdominal placement include the risk of development of a pouch hematoma, infections of the pouch and the outlet region, wound dehiscence and erosion of the skin over the implanted device. Possible complications of the intra-abdominal method of implantation may include membrane hernia of the pericardium, wound dehiscence, abdominal (intestinal) adhesions, intestinal blockage, erosion of the stomach, the rectum, and liver and internal organs of the abdominal chamber. The use of the skin coring punch can be a more traumatic method, which can lead to unsatisfactory healing of the wound surface. The device has a flexible silicon sleeve, which during creation of a small pump pouch may lead to its angulation, this causing an obstruction at the level of the inflow cannula. According to some authors [Taghavi S., Ward C., Jayarajan S. N., Gaughan J., Wilson L. M., and Mangi A. A. Surgical Technique Influences HeartMate II Left Ventricular Assist Device Thrombosis. Ann Thorac Surg 2013; 96:1259-65], the angle of the inflow cannula must be greater than 55% to minimize the risk of development thrombosis risk of the HeartMate II device. A deficiency of the above-described technique of placing sutures for implantation of the sewing cuff is twisting of the incision edges inside the left ventricular chamber, which can lead in the future to obstruction of the inflow cannula.

The closest prior art is a method of implantation of the left ventricular mechanical indicated by the developer of the device [HeartMate III Left Ventricular Assist System Instructions for Use. Thoratec Corporation, 2014. Document: 109798.B]. HeartMate III devices are positioned intrapericardially. First the driveline is tunneled, leaving as much of the velour surface of the cable on the inside. A 6-mm coring device is used for perforation of the skin. An anastomosis between the outflow graft and the ascending aorta. The patient is connected to the CPB pump. Select the site for the inflow cannula slightly anterior to the apex and a few centimeters lateral to the anterior to the interventricular artery. Using a scoring punch, cut a round opening in the left ventricle. For sewing the cuff, the techniques of "cut then sew" or "sew then cut" may be used. Place at least 12 horizontal mattress sutures with synthetic pledgets through nearly the entire thickness of the myocardium at a distance of 1.5 cm from the edge of the incision. Sew the sewing cuff and place the device in the left ventricle. Connect the outflow graft to the device. Perform de-airing, activate the HeartMate III device, and switch off the CPB apparatus.

A drawback of this method is the fact that it can be used in the capacity of recommendations, but does not have sufficient clinical information. First of all, the use of the skin coring punch can be a more traumatic method, which can lead to unsatisfactory healing of the wound surface, and the anatomic selection of the site of implantation of the inflow cannula (without check of visualization using a transesophageal echocardiogram), as was described above for implantation of other types of devices. Second, the technique of placing sutures during sewing of the apical sewing cuff is not adequately described. Third, anastomosis between the outflow graft and the and the ascending aorta is created prior to placement of the pump, which subsequently may lead to incorrect length of the graft and technical difficulties in connecting the graft to the device.

GENERAL DESCRIPTION

At present there is a tendency toward an increase in implantation of HeartMate III devices in many countries, including the Republic of Kazakhstan and the United States of America.

The object of the invention is to raise the effectiveness of the implantation of the HeartMate III left ventricular mechanical assist device by reducing postoperative complications to a minimum and improving long-term results of device operation.

BRIEF DESCRIPTION OF THE DRAWINGS

The patent or application file contains at least one drawing executed in color. Copies of this patent or patent application publication with color drawings will be provided by the Office upon request and payment of the necessary fee.

DETAILED DESCRIPTION OF THE EMBODIMENTS

Figure 1:
FIG. 1 illustrates the first step in the hemostatic and non-obstructive technique of placing sutures for implantation of a sewing cuff. This figure shows the first perforation of the needle is through the entire thickness of the myocardium at a distance of around 1-1.5 cm from the edge of the incision.

Based on clinical results from the use of various types of devices by the authors of the invention, a new method has been developed for implantation of the HeartMate III left ventricular mechanical assist device, which includes the following sequence of actions.

A round opening is made using a scoring punch. The left ventricle must be cleared of potential sources of obstruction (thrombi etc.). Then a "hemostatic and non-obstructive technique" of implantation of the sewing cuff is carried out, tunneling of the driveline with externalization of the silicone part. A correct length is selected for the outflow graft. Fixation of the bend relief after creation of the anastomosis between the outflow graft and the ascending aorta, which makes it possible to avoid graft kinking. In all stages of implantation, correct de-airing is carried out. The speed of the device is selected such that there is adequate unloading of the left ventricle, the interventricular septum is arranged evenly, there is no overloading of the right ventricle, and opening of the aortic valve with every heart contraction is ensured. The external part of the cable is affixed.

The method is presented with the principles of implantation and is implemented as follows.

Surgical stages of implantation of the HeartMate III left ventricular mechanical assist device are:

1) Median sternotomy.
2) Opening of the pericardium.
3) Device assembly: connect outflow graft to the pump before implantation, which is more convenient for selecting its length. Operation of pump must be checked prior to implantation.
4) Connect to CPB.
5) Implantation of left ventricle mechanical assist device with parallel artificial circulation, which makes it possible to manipulate the heart during the time of the operation safely and with satisfactory exploration. During additional surgical correction (repair/prosthesis of heart valves, coronary shunt etc. blood cardioplegia solution is used.
6) While monitoring with transesophageal echocardiogram, select the site for placement of the inflow cannula.
7) Using a scoring punch, cut a round opening.
8) Sew the sewing cuff with pi-shaped sutures with synthetic pledgets.
9) Connect the device to the sewing cuff and place intrapericardially.
10) Tunneling of the driveline. Run the cable with a standard straight-line or "C-shaped" (double tunnel) shape.
11) Create the anastomosis between the outflow graft and the ascending aorta.
12) Activation of the artificial left ventricle. Prophylaxis of the air embolism under monitoring by means of transesophageal echo cardiography.
13) Fixation of bend relief after creation of the anastomosis between the outflow graft and the ascending aorta.
14) Then gradually increase the speed of the device and disconnect the patient from the CPB apparatus.
15) Device speed is selected such that there is adequate unloading of the left ventricle and the interventricular septum is even.
16) Hemostasis. A xenopericardial patch is fixed to the edges of the pericardium if a heart transplant is planned for the patient in the future. The ribcage is sutured in layers.
17) Fixation of the driveline.

Principle 1. De-airing of the assembled HeartMate III device during its testing prior to implantation. A physiological solution is injected through the outflow graft and into the pump. During device testing in the physiological solution, it is necessary to shake carefully.

Principle 2. Positioning of the inflow cannula—"finger test." Technique "cut then sew." Under monitoring by transesophageal echocardiography, by the finger test select the site for placement of the inflow cannula. Anatomically this region is located on the anterolateral wall of the left ventricle at a distance of roughly 1-1.5 cm from the apex and from the left anterior descending artery depending on the dimensions of the left ventricle. The "cut then sew" technique makes it possible to better visualize the left ventricular chamber for eliminating potential causes of obstruction of the inflow cannula, and also allows use of the "hemostatic and non-obstructive technique" of sewing cuff implantation. Using the scoring punch, create a circular incision. Remove thrombi from the left ventricular chamber if present. Chords and trabeculae that may potentially cause obstruction of the inflow cannula must be excised. The inflow cannula must be placed parallel to the interventricular septum and the direction of its axis must be projected in the direction of the mitral valve, being thus disposed between the interventricular septum and the lateral wall of the left ventricle.

Figure 2:
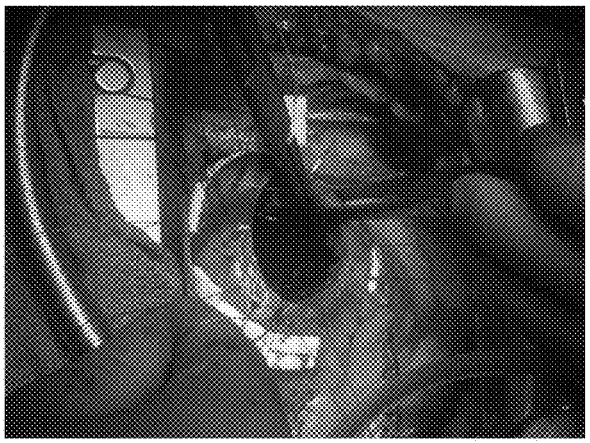
FIG. 2 illustrates the second step in the hemostatic and non-obstructive technique of placing sutures for implantation of the sewing cuff. The second perforation of the needle, returning back, passes through the middle of the thickness of the myocardium on the outside at a distance of 5 mm from the edge of the incision.
Figure 3:
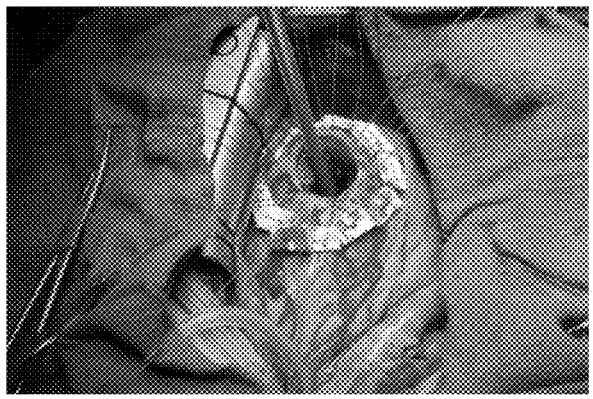
FIG. 3 illustrates a final view of the sutures placed on the myocardium of the left ventricle in the hemostatic and non-obstructive technique of placing sutures for implantation of the sewing cuff.

Principle 3. "Hemostatic non-obstructive technique" of sewing cuff implantation. Reference is made to FIGS. 1, 2 and 3 illustrating how the invention is used in the hemostatic and non-obstructive technique of placing sutures for implantation of the sewing cuff. When there are sources of bleeding from branches of the coronary arteries, sutures are placed so as to prevent bleeding in the postoperative period. Twelve Π-shaped sutures of Ethibond 3-0 with synthetic pledgets are used, ensuring effective use of the below-described technique of sewing cuff implantation. The first perforation of the first needle passes through the entire thickness of the myocardium at a distance of around 1-1.5 cm from the edge of the incision (FIG. 1), and then, the second perforation of the needle, returning back, passes through the middle of the thickness of the myocardium on the outside at a distance of 5 mm from the edge of the incision (FIG. 2). The second needle performs the same maneuver. At the end of suturing on the myocardium (FIG. 3), the device sewing cuff is sewn. When the sutures are tied, the pledgets must be on the outside of the sewing cuff and not under it. This technique makes it possible to adequately seal the fixation region of the sewing cuff and thus minimize the probability of bleeding. In addition, sewing of the myocardium through its entire thickness fixes the edges from the direction of the left ventricular chamber, thus eliminating potential risks of obstruction of the inflow cannula, especially in patients with myocardial hypertrophy of the left ventricle. Additionally, check for hemostasis. With a finger close the opening; the left ventricular chamber will fill with blood, then check the seal of the sewing cuff.

Principle 4. Tunneling of the driveline with externalization of the silicone part. Run the cable in a standard straight line if a subsequent heart transplant is planned for the patient (BTT—"bridge to transplantation"—or in a "C" shape (double tunnel) if the device is to be used as a "destination therapy"). The skin incision is made longitudinally with a scalpel instead of using a skin coring punch. The driveline is run out in such a way that the transitional part of the velour is in silicone to a depth of more than 1 cm from the surface of the skin. With straight tunneling of the driveline, it is possible to leave its loops intrapericardially in order to preserve the principle of externalization of the silicone part.

Principle 5. Correct length of outflow graft. Stretching of the outflow graft is done prior to implantation of the device. The length is chosen such that it is not too short, since this can cause compression of the right atrium and right ventricle, and not too long, which can lead to bending of the outflow graft. The incision of the ascending aorta is made maximally proximally in the event that a heart transplant in the future is planned, but superiorly to the sinotubular junction, and on the anterolateral wall of the aorta. Lateral formation of the anastomosis may provoke compression of the superior vena cava. The incision of the outflow graft must be at an acute angle of 30-45°, which will ensure conformity of the direction of blood flow through the outflow graft with the direction of blood flow in the aorta. For creating the anastomosis, ProleneHemo-Seal 4/0 sutures are used to minimize blood flow through the perforations of the needle.

Principle 6. Fixation of the bend-relief after creation of the anastomosis Between the outflow graft and the ascending aorta, which makes it possible to avoid the kinking of the outflow graft.

Principle 7. De-airing before and after creating the anastomosis between the outflow graft and ascending aorta. After connecting the pump to the sewing cuff and tunneling of the driveline, de-airing is carried out with a temporary reduction in the speed of the CPB and forcing out the air with blood flow through the outflow graft. After formation of the proximal anastomosis, before removal of the vascular clamp from the outflow graft, the function of the artificial left ventricle is activated, and a needle is used with monitoring by transesophageal echocardiography to prevent an air embolism.

Principle 8. Speed of the device and CPB cutoff. The speed of the left ventricular mechanical assist device and a reduction in the CPB. The speed of the device is selected such that there is adequate unloading of the left ventricle, the interventricular septum is even, there is no overload of the right ventricle, and the aortic valve is opened with every heart contraction.

Principle 9. Fixation of the driveline. The internal part of the driveline is not fixed so as to ensure some mobility in the case of patient weight gain, in order to avoid deformation of the driveline. The external part of the driveline is fixed to the skin using a silicone tube around 10 cm long and two sutures for 1 month, which ensures satisfactory healing of the output region of the driveline by maintaining its immobilization.

Examples of method implementation.

Example 1

A 60-year-old patient presented on May 4, 2016 to the NKKTs with the diagnosis "Primary: coronary heart disease. Two-vessel coronary bed lesion. Myocardial infarction (2006, December 2015). Complications: Ischemic cardiomyopathy. Thrombosed aneurysm of the left ventricle. Complete left bundle-branch block. Atrial fibrillation, paroxysmal form. European Heart Rhythm Ass. III. Chronic heart failure, NYHA 3, stage D (AHA/ASS INTERMACS 4."

One May 13, 2016 patient underwent surgery "thrombectomy of left ventricle, implantation of HeartMate III left ventricular mechanical assist device under CPB conditions (parallel perfusion)."

Intraoperative TEE: "Dilatation of the left ventricle. End-diastolic volume of the left ventricle=250 ml. Ejection fraction of the left ventricle=15%. Walls of the left ventricle—thick endocardium, apical thrombus, 3.2*3.6 cm, continues to the intraventricular septum and the lateral wall of the left ventricle.

Left atrial appendage free of thrombi. "Water" test negative—open oval window not identified. Function of the right ventricle satisfactory." Median longitudinal sternotomy. Pericardial chamber is opened. Cannulation of the aorta, right atrium. CPB started, operation continued in parallel perfusion. Under monitoring of transesophageal echocardiography, an optimal region for is implantation of the inflow cannula is selected. Using the skin coring punch, an opening is made in the region of the apex of the left ventricle. A sample of the myocardium is sent for histologic investigation. Careful resection of the chamber of the left ventricle in search of a thrombus—thrombus discovered lining the chamber of the left ventricle. Thrombectomy of the left ventricle performed. Prevention of material embolism.

Using 12 pi-shaped sutures (Ethibond sutures) with synthetic pledgets, the sewing ring cuff is implanted. Ventricular fibrillation. Rhythm restored to sinus after 1 discharge of the defibrillator. An optimal orientation of the pump was selected on the apex of the left ventricle, which is tightly secured to the sewn apical ring. Tunneling is carried out, the cable is moved to the right (conventional technique), the silicone portion of the driveline's surface (silicone part on the outside)). The aorta is pressed toward the wall, using a continuous Prolene 4/0 suture, an and-to-side anastomosis is formed between the outflow graft and the ascending aorta. Prevention of an air embolism by insertion of a drainage needle into the region of the drain implant. Blood flow initiated at a speed of 3000 rpm. Termination of CPB. Pump speed increased to 4800 rpm. Transesophageal echocardiography: "Interventricular septum—disposed evenly. Inflow cannula aimed in the direction of the mitral valve." Sinus rhythm, heart rate=40 bpm. Electrodes sewn to the right ventricle for temporary pacemaking. Rhythm established by pacemaker with ventricular contraction rate=80 bpm. Decannulation of the aorta and right atrium. Meticulous hemostasis. Drainage of the left pleural cavity and anterior mediastinum. Layered suturing of the chest. Iodine on wound. Aseptic dressing. Blood loss 200 ml.

Duration of CPB=100 minutes. Pump speed=4800 rpm. Pump flow=3.8. PI=3.4.

Patient extubated the same time. On May 21, 2016 patent was transferred from the resuscitation and intensive care ward to the cardiac surgery ward. In the postoperative period episodes of atrial fibrillation were noted, which were restored to sinus rhythm by administration of Amiokordin. On May 25, 2016 patient was transferred in relatively satisfactory condition to the rehabilitation ward. on Jun. 4, 2016 patient was discharged from the NNKTs under the observation of a cardiologist and VAD (ventricular assist device) coordinator for his place of residence. At the moment of discharge the sternum was stable, healing of the postoperative wound was per primam. At present the HeartMate III device is operating satisfactorily. There has been no development of infection complications in the region of driveline exit.

The proposed method of implantation of the HeartMate III left ventricular assist device makes it possible to minimize the surgical causes of device thrombosis and bleeding, to avoid kinking of the outflow graft, and to reduce the incidence of infection complications of the driveline exit region, and thus to improve the long-term results of device operation.

The invention claimed is:

1. A method of implantation of a left ventricular assist device including placement of the device in the left ventricle of a patient, comprising:
   connecting the patient to a parallel cardiopulmonary bypass (CPB);
   performing the following steps;
   (i) while monitoring the patient by transesophageal echocardiography, selecting a site for placement of an inflow cannula,
   (ii) implanting a sewing cuff using pi-shaped sutures with synthetic pledgets, by sewing through an entire thickness of the myocardium thereby fixing edges of the sewing cuff at a left ventricular chamber side, such that when the sutures are tied the pledgets are completely on an outside of the sewing cuff thereby adequately sealing a fixation region of the sewing cuff to minimize probability of bleeding,
   (iii) connecting the device to the sewing cuff and placing the device intrapericardially,
   (iv) tunneling a driveline by making a skin incision longitudinally with a scalpel for improving healing of an output region of the driveline, and leaving a loop of the driveline intrapericardially to maintain externalization of a silicone part of the driveline,
   (v) creating an anastomosis between an outflow graft and ascending aorta, while performing de-airing prior to and after said anastomosis, and affixing a bend-relief after the creation of the anastomosis between the outflow graft and the ascending aorta, to avoid kinking of the outflow graft, (vi) after formation of proximal anastomosis, and prior to removal of a vascular clamp from the outflow graft, activating the left ventricular assist device disconnecting the CPB from the patient.

2. The method according to claim 1, wherein said selecting a site for placement of the inflow cannula and said sewing of the sewing cuff is performed by using a technique of "cut then sew".

3. The method according to claim 1, wherein said implantation of the sewing cuff is performed by a hemostatic and non-obstructive technique comprising:

forming a first pair of first and second perforations by a first needle performing a maneuver, wherein the first perforation is formed by the needle passing through the entire thickness of the myocardium at a distance of about 1-1.5 cm from an edge of the incision, and is followed by the second perforation formed by the needle, which while returning back, passes through a middle of the thickness of the myocardium on the outside thereof at a distance of about 5 mm from the edge of the incision; and forming a second pair of the first and second perforations using a second needle performing said maneuver.

4. The method according to claim 1, wherein an operational speed of the device is selected with allowance for adequate unloading of the left ventricle and an even position of the interventricular septum.

5. The method according to claim 1, wherein in order to avoid deformation of the driveline, an internal part of the driveline is not fixed, so as to ensure some mobility in the event the patient gains weight, and an outside part of the driveline is fixed to the skin using a silicone tube around 10 cm long and two sutures for a 1 month time period.

* * * * *